US008330958B2

(12) United States Patent  
Levitsky

(10) Patent No.: US 8,330,958 B2  
(45) Date of Patent: Dec. 11, 2012

(54) DEVICES FOR OPTOCHEMICAL DETECTING OF VAPORS AND PARTICULATES USING POROUS PHOTONIC CRYSTALS INFILTRATED WITH SENSORY EMISSIVE ORGANICS

(75) Inventor: Igor A. Levitsky, Fall River, MA (US)

(73) Assignee: Emitech, Inc, Fall River, MA (US)

( * ) Notice: Subject to any disclaimer, the term of this patent is extended or adjusted under 35 U.S.C. 154(b) by 315 days.

(21) Appl. No.: 12/702,143

(22) Filed: Feb. 8, 2010

(65) Prior Publication Data

US 2011/0194115 A1 Aug. 11, 2011

(51) Int. Cl.
*G01N 21/00* (2006.01)

(52) U.S. Cl. ........................................ 356/442
(58) Field of Classification Search .................. None
See application file for complete search history.

(56) References Cited

U.S. PATENT DOCUMENTS

| 6,686,206 | B2 | 2/2004 | Levitsky |
| 7,208,122 | B2 | 4/2007 | Swager |
| 7,393,503 | B2 | 7/2008 | Swager |
| 7,419,636 | B2 | 9/2008 | Aker |
| 2006/0199260 | A1* | 9/2006 | Zhang et al. ............... 435/293.1 |

OTHER PUBLICATIONS

Walt et al., Chem. Rev. 100: 2595, 2000.
Grate, Chem. Rev. 100: 2627, 2000.
Swager et al., J. Am. Chem. Soc. 120: 11864, 1998.
Levitsky et al., J. Phys. Chem. B 105: 8468, 2001.
Zang et al., J. Am. Chem. Soc. 129: 6978, 2007.
Su et al., Synth. Met. 144: 297, 2004.
Trogler et al., Angew. Chem. Int. Ed. 40: 2104, 2001.
Li et al., Colloid. Polym. Sci. 285: 721, 2007.

* cited by examiner

Primary Examiner — Tu Nguyen

(57) ABSTRACT

An optochemical detector for detecting various chemical compounds and comprising a flow cell incorporating the sensory element constructed of an organic-inorganic emissive nanocomposite which luminescence spectral response is specific to exposed target vapors and particulates. The change in the luminescent spectral response is measured during this exposure. The detector is equipped with air-jet sampling system functioning in real-time mode for delivery of vapors and particulates to sensory element.

28 Claims, 6 Drawing Sheets

DEVICES FOR OPTOCHEMICAL DETECTING OF VAPORS AND PARTICULATES USING POROUS PHOTONIC CRYSTALS INFILTRATED WITH SENSORY EMISSIVE ORGANICS

STATEMENT REGARDING FEDERALLY SPONSORED RESEARCH OR DEVELOPMENT

This invention was made with Government support under U.S. Army No. W56 HZV-07-C-0150. The Government may have certain rights in the invention.

FIELD OF THE INVENTION

The present invention describes the device design and its functions for the precise detection and identification of target vapors and particulates with the use of porous semiconductors infiltrated with emissive sensory organics. This invention discloses both the major principle of the analytes detection and identification by the optochemical detector and the detailed device construction comprising the functional modules.

BACKGROUND OF THE INVENTION

The research and development of new MEMS technologies and electronic materials for the detection of toxic and explosive vapors with high sensitivity and selectivity is of utmost importance for many commercial, environmental, security applications and for US military missions.

Detection techniques include a variety of physical and chemical methods related to changing the output signal under exposure to target analytes. Physical methods include: nuclear quadrupole resonance, ion mass spectroscopy, gas chromatography, X-ray diffraction, electron capture detection, and laser photofragmentation. These techniques are selective enough, but can be expensive, bulky and cannot be employed for fast, real-time, and remote analyte detection. Also, most of the chemical sensors have been studied, developed, and fabricated in the macro format using traditional techniques for the deposition of sensory polymers (spin-casting, coating, spraying) onto relatively large area substrates followed by coupling to a separate detection/acquisition system (Walt et al., Chem. Rev. 100: 2595, 2000; Grate, Chem. Rev. 100: 2627, 2000). Such devices could be employed for pattern recognition of vapor mixtures. However, vapor concentration should be high enough to prevent a false response and to correctly identify the explosive chemical signature. Since many toxic and explosive vapors (for example, TNT, RDX, PETN) are related to low pressure vapors, the critical issue becomes an enhancement of sensor sensitivity and selectivity to provide a fast, real-time response with a minimum false alarm.

The series of articles and patents by Swager et al. (J. Am. Chem. Soc. 120: 11864, 1998; U.S. Pat. Nos. 7,208,122 and 7,393,503) propose a new concept, namely the "molecular wire" approach, related to emissive optochemical sensors for the detection of explosive vapors. The major issue here is the amplification mechanism based on an energy migration effect allowing very high device sensitivity, which is of utmost importance for the detection of explosives with a low pressure of saturated vapors. U.S. Pat. No. 6,686,206 and an article (J. Phys. Chem. B105:8468, 2001) by Levitsky et al. also describes the optochemical sensors involving amplification mechanism of luminescence, however it is based on the direct Forster energy transfer. Despite possessing high sensitivity, the above emissive sensors suffer low selectivity as quenching or enhancing of the emission demonstrates similar behavior for different parts of the luminescent spectrum.

U.S. Pat. No. 7,419,636 (Aker et al.) describes an instrument for the detection of explosives using fluorescence quenching of amplifying polymers as a transduction mechanism. U.S. Pat. Nos. 7,208,122 and 7,393,503 (Swager et al.) describe the method to synthesize fluorescence amplifying polymers for nitroaromatic explosive detection. Note, that other amplifying polymers (which are not subjected to U.S. Pat. Nos. 7,208,122 and 7,393,503), small emissive molecules and oligomers can also be sensitive to nitroexplosive (see L. Zang, et al. J. Am. Chem. Soc. 129: 6978, 2007; A. Su, et al. Synth. Met. 144: 297, 2004; W. C. Trogler, et al. Angew. Chem. Int. Ed. 40: 2104, 2001; G. Li, et al. Colloid. Polym. Sci. 285: 721, 2007). All of these species (emissive sensory organics) can be infiltrated inside one-dimensional porous photonic crystal with microcavity (MC) forming a novel nanocomposite emissive material with advanced sensory characteristics to explosive vapors and particulates. The method of explosive and other low pressure vapors detection using MC based emissive nanomaterials has been described in the U.S. patent application Ser. No. 12/051,233 (Levitsky). This method has serious advantages over traditional fluorescence quenching because of the additional sensory parameter: MC spectral shift upon vapor exposure. As a result, an enhanced selectivity can be achieved. Also, nanoporous structure of photonic crystal results in much higher surface area (ranging from 200 to 800 $m^2/cm^3$), which provides numerous sites between the sensory material and the analyte vapors. This increases sensitivity and reduces response time. The method described in the U.S. patent application Ser. No. 12/051,233 was not implemented in the design of a real device capable to detect low concentrated vapors and particulates in the real-time mode and also vapors with moderate and high vapor pressure. Also, in this application nothing has yet been disclosed about real-time sampling system and no details were presented about the preparation of the MC based emissive sensory material.

It would therefore be desirable to have a thoughtful description of the sensory device (including sampling system) for optochemical detection vapors and particulates using MC based emissive composite materials.

SUMMARY OF THE INVENTION

The present invention relates to a system for detecting vapors and particulates of various chemicals which includes but not limited to explosives, chemical warfare agents, toxic organic and inorganic compounds. A major group of interest is nitroexplosives such as TNT, RDX, and PETN, possessing extremely low pressure of saturated vapors (ppt-ppb range) and their interferants with moderate and high vapor pressure (non-explosive compounds similar to explosives), however any other groups of the chemicals can also be detected and identified.

The present invention also provides the method and related instrumentation for analyte sampling and delivery to the sensory element. Analyte refers to three categories: vapors of interest containing in the air; particulates of interest desorbed by the sampling system and delivered with the air to the sensory element; vapors of interest in the air, which are the result of analyte particulates evaporation affected by the thermal air-jet incorporated in the sampling system.

The present invention also provides the method of fabrication of sensory element comprising one-dimensional porous photonic crystal with microcavity (MC) infiltrated with sensory emissive organics. As a result of such composite formation, a broad luminescent band of the emissive organics narrows to the sharp luminescence peak, in which the intensity and the spectral position are sensitive to the presence of the analyte.

The present invention also provides the device for analyte detection and identification which comprises the sensory element with composite based sensory emissive material, flow cell with sensory element, pump for analyte delivery to the sensory element through the flow cell, source of excitation of the sensory emissive material, mini-spectrometer for spectral change recording upon analyte exposure, microprocessor controlling device functions and data exchange, and processing algorithm providing data processing, analyte quantitation and classification.

DETAILED DESCRIPTION

Optochemical sensors (or optodes) based on specially designed sensory polymers specific to the target vapors blended with solvatochromic dyes (optical transducers) or polymers with their own luminescence have received much attention for the past decade (see refs. to Swager's and Levitsky's papers in the "background of invention" section). In addition, luminescence of small molecules itself or incorporated in the sol-gel also can be sensitive to different groups of vapors. Such sensors demonstrated high sensitivity (ppt-ppb range). Nevertheless, their selectivity suffers due to a lack of precise detection of the spectral shift and intensity change under analyte exposure because of the broad spectral band of the solvatochromic dyes or conjugated emissive polymers (FWHM ~100-150 nm).

In the U.S. patent application Ser. No. 12/051,233 a method of detecting low pressure vapors is disclosed, using one-dimensional porous photonic crystal with MC (further named MC only) infiltrated with emissive sensory organics to provide high sensitivity (luminescence quenching or enhancement) and high selectivity as a result of change of the MC refractive index. It is important that the luminescence of such composite emissive sensory material (CSEM) demonstrated a significant narrowing of the broad luminescence band to a sharp peak due to photon confinement in the MC structure. Upon analyte exposure, CSEM luminescent peak exhibits not only luminescence quenching (or enhancement) but also a spectral shift due to the change of the refractive index of porous MC as a result of binding of analyte molecules to sensory emissive organics. Thus, the selectivity of the analyte detection significantly increases because of an additional parameter (spectral shift) introduced in the detection and classification protocol.

The presented invention mostly relates to the device for sampling and detection of low concentrated vapors and particulates, however other issues (which were not disclosed in the U.S. patent application Ser. No. 12/051,233) related to CSEM fabrication and sensing of moderate/high concentrated vapors are presented herein.

Figure 1:
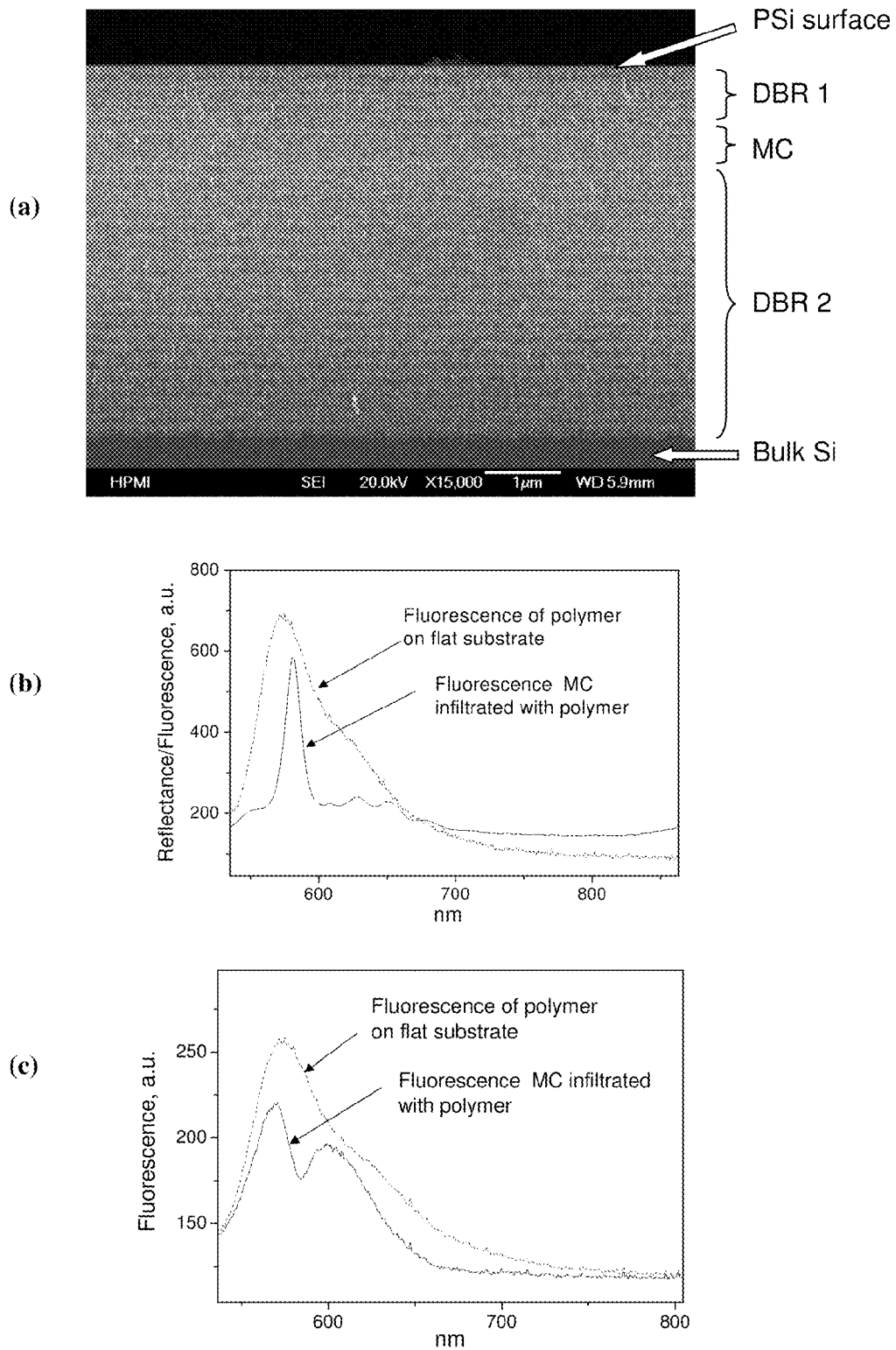
FIG. 1A shows the cross-sectional SEM image of a DBR1/MC/DBR2 nanoporous Si structure (one-dimensional porous photonic crystal with microcavity (MC)). First distributed Bragg reflector (DBR1) and second DBR2 contains 5 and 20 periods of porous silicon multilayers of high (59%) and low porosity (43%). The 200 nm thick MC layer is between DBR1 and DBR2.
FIG. 1B shows fluorescence spectrum of MEH-PPV after deep infiltration inside MC (solid line). For comparison MEH-PPV on a flat substrate (dashed line) is presented.
FIG. 1C shows fluorescence spectrum of MEH-PPV after shallow infiltration inside MC (solid line). For comparison MEH-PPV on a flat substrate (dashed line) is presented.

The U.S. patent application Ser. No. 12/051,233 demonstrated only the result of deep infiltration of sensory emissive organics inside nanoporous MC resulting in the narrow luminescent peak of CSEM but did not disclose the corresponding method of CSEM fabrication. FIG. 1 shows the SEM image of the cross-section of porous silicon MC and CSEM photoluminescent spectra as a result of deep (FIG. 1b) and shallow (FIG. 2c) MC infiltration with emissive sensory polymer poly(2-methoxy-5-(2-ethyl-hexyloxy)1,4-phenelynevinylene) (MEH-PPV). The critical condition for deep and uniform MC infiltration is the appropriate sequence of L/H/

Figure 3:
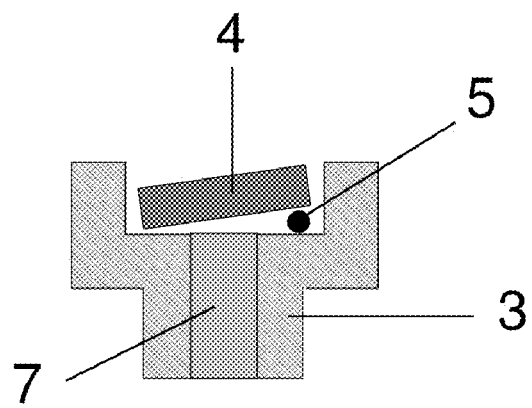
FIG. 3 illustrates the schematic of the removable cartridge (enlarged area in the dashed circle from FIG. 2) with sensory element, tilting mechanism and ultrasound transducer.

L/H . . . . Low (L)/High (H) porosity layers with the L porosity layer on top (FIG. 1b). The reversal sequence such as H/L/H/L . . . results in shallow polymer infiltration (FIG. 1c) resulting in the spectral "hole" in the broad luminescent band of MEH-PPV. Presumably such effect can be associated with the higher capillary forces in the first L porosity layer, which dominates in the filling process. The followings are the steps required for deep infiltration of sensory emissive organics inside the nanoporous MC structure: (i) Deposit MEH-PPV in chloroform solution on MC surface; (ii) Let polymer solution cover whole MC area for at least 30 s, allowing the polymer to be infiltrated inside MC pores due to capillary forces; (iii) spin cast (3000-5000 rpm for 20 s) the sample to remove excess polymer solution from MC surface; (iv) anneal the resulting CSEM in oven at 80° C. for 30 min; (v) cut the CSEM to the appropriate size (3 mm×4 mm) to fit the pocket in the cartridge 3 (FIG. 3). In the followings, the term CSEM means the same as the sensory element 4 (FIG. 3).

Figure 2:
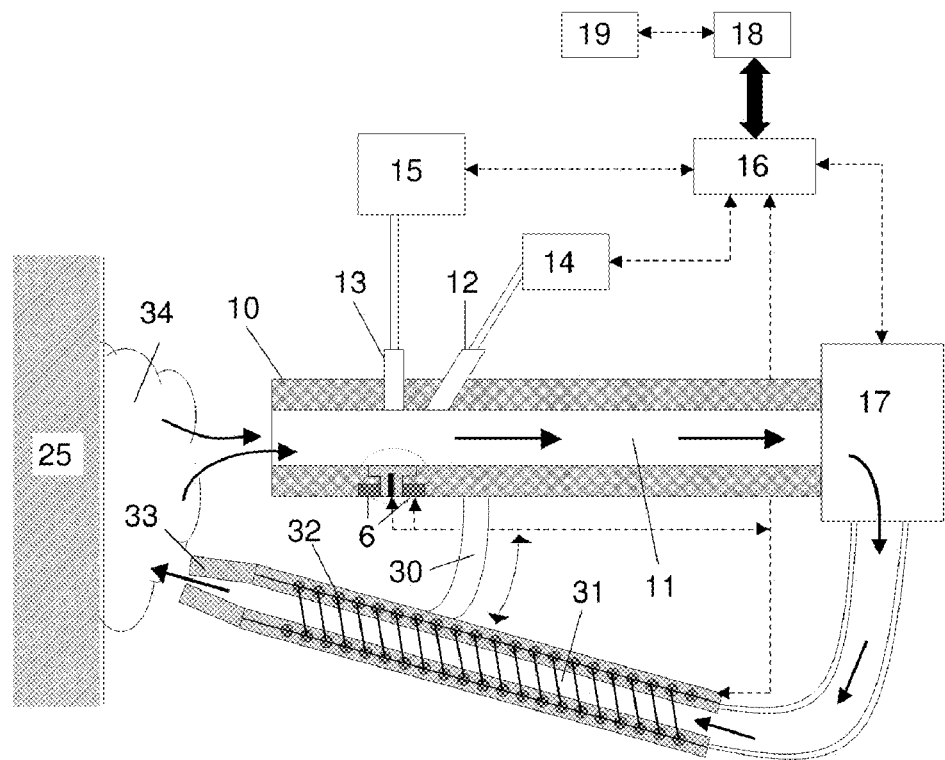
FIG. 2 illustrates the schematic of the detector in accordance with the present invention.

FIG. 2 and FIG. 3 show the principle design of the detector based on the presented invention. The detector is constructed from a flow cell 10 comprising of the cartridge 3 with sensory element 4 and connected to a pump 17 to provide air flow containing the analyte molecules (vapors and/or particulates) through the flow channel 11. The sensory element (SE) 4 senses the analyte molecules interacting with the sensory emissive organics inside the porous MC, resulting in the spectral change of the SE luminescence. The flow cell 10 further comprises of two optical fibers 12 and 13, positioned and fixed in the wall of the flow channel 11, to excite and collect luminescence from SE 4. Optical fiber 13 is coupled with a mini-spectrometer 15 to detect luminescence spectrum of SE and its temporal change upon analyte exposure. Optical fiber 12 is coupled with a light-emitting diode 14 emitting light in the range of 350-420 nm, where the most luminescent sensory organics possess absorption band. The device is further comprises of an air-jet sampling system 31 constructed from a multi-layer concentric ceramic tubes heated by metal coils 32 and functioning at elevated temperatures from 50° C. to 250° C. The tube of the smallest diameter of the air jet is connected to the exhaust of pump 17 to provide multiple analyte cycling through the flow channel with sensory element, smallest tube of the air-jet and inspected area. The air-jet directs the flow of the heated air to the inspected surface 25 so that the desorbed analytes 33 (particulates and/or vapors) can be introduced to the inlet of the flow channel 11. Thus, analyte sampling occurs in real-time mode in parallel with analyte detection. The air jet further comprises of a narrow tip 33 for focusing/defocusing the air flow and a movable console 30 which allows varying the direction of the air flow. The detector further comprises of a data acquisition system (DAQ) 15, a microprocessor (MP) 18 and a graphic user interface (GUI) 19. DAQ provides data exchange between the spectrometer 15 and the MP 18. The microprocessor through the DAQ is able to control the functions of other detector modules (LED, pump, heaters). The MP runs a processing algorithm to analyze the output signals and display the results on the GUI 19; the sign "clear" in the case where the target analytes are absent or the sign "analyte X" in the case of the presence of analyte X, wherein the analyte X is from the group of target analytes.

It has been determined that the width of the flow channel 11 and tilt of the sensory element 4 with respect to the air flow direction play important role for enhanced sensitivity. The flow at the higher width than optimal size cannot supply enough analyte molecules to the SE surface, as many of them passes by SE without interacting with the SE. While the channel width, which is less the optimal size, results in the reduction of the flow rate. An optimal width lies in the range of the 0.2-0.4 mm at a flow rate of 600 ml/min. However, higher flow rates may result in smaller width of the flow channel. Also, it was found that a small tilt of SE relative to the flow direction additionally enhances the detector sensitivity. FIG. 3 shows the means 5 for SE tilt regulation. Preferably the tilt angle should be in the range of 3-4 degree relative to the horizontal SE position for the thickness of the flow channel of 0.3 mm. However, other preferable angles may exist for smaller optimal widths of the flow channel. Such effect can be explained by the higher analyte sorption when the analyte molecules impact the surface of SE.

In some embodiments, the cartridge with sensory element may be surrounded by a heating/cooling mini-device 6, comprising of a mini-heater, a mini-thermoelectric cooler and a temperature sensor (thermistor) to regulate the temperature of the SE in the range of 5° C.-100° C. through the DAQ and the appropriate software. The temperature difference between the analyte in the flow channel and the SE can be an important issue during the analyte sorption and desorption cycles. For efficient sorption, the temperature of the SE surface should be lower than the temperature of the analyte molecules. In contrast, to provide analyte desorption from the SE in clean air (sensor recovery mode), the temperature of the SE should be higher than the temperature of the flowing air.

Figure 4:
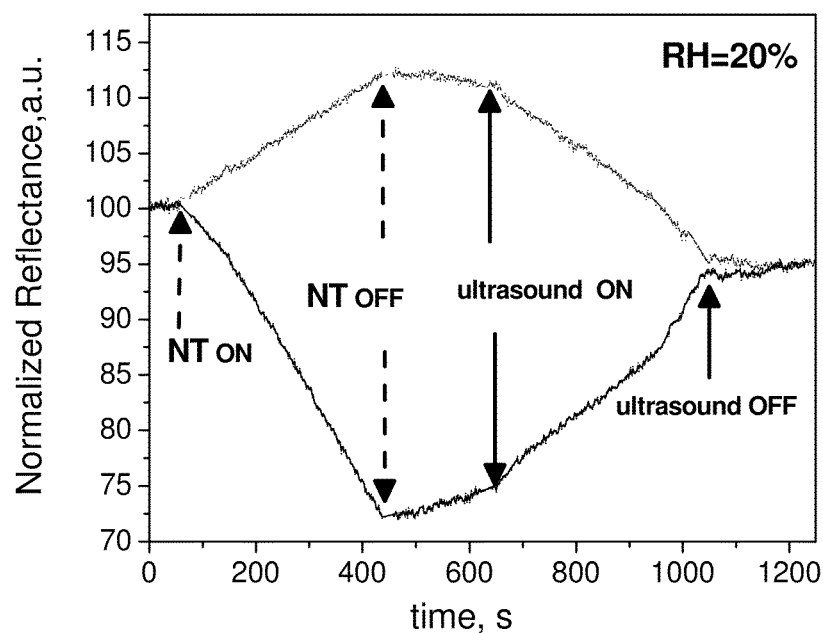
FIG. 4 shows time traces of the normalized reflectance upon exposure of saturated vapors of nitrotoluene (NT) followed by 125 mW ultrasound ON/OFF cycle. Reflectance intensities were taken on the half of the width of MC peak for short wavelength/left (dashed) and long wavelength/right (solid) shoulders.

In another embodiment, the cartridge with the sensory element comprises of an ultrasound transducer 7 (FIG. 3) to provide further desorption (removal) of analyte molecules from the SE surface in the recovery mode. Previous experimental work showed that ultrasound facilitates removal of vapors adsorbed by the porous MC. FIG. 4 demonstrates the dynamics of porous Si MC peak spectral position (time traces of the normalized reflectance measured on the left and right shoulder of the peak) upon exposure of saturated nitrotoluene vapors followed by ultrasound application. Without ultrasound, the natural recovery takes about 30 minutes, while with ultrasound the recovery time does not exceed 5-6 minutes.

In the present invention, emissive sensory organic materials entrapped inside the porous MC may include: any emissive sensory conjugated polymers (except polymers with structure disclosed in U.S. Pat. Nos. 7,208,122 and 7,393,503), emissive sensory molecules or quantum dots; organic emissive molecules or quantum dots blended with non-emissive sensory polymers; emissive sensory molecules or quantum dots entrapped in sol-gel matrixes; emissive sensory molecules forming j-aggregates in the solid films, etc. Examples of emissive sensory conjugated polymers are poly[p-phenylenevinylene] (PPV); poly[2-methoxy-5-(2-ethylhexyloxy)-pphenylenevinylene] (MEH-PPV); poly(2,3-diphenyl-5-n-decyl-p-phenylenevinylene) (DP10-PPV); poly[1-(p-n-butylphenyl)-2-phenylacetylene] (BuPA); emissive sensory molecules are porhyrines and phtalocyanines derivatives, solvatochromic dyes such as Nile Red and Nile Blue and other emissive molecules and dyes; emissive sensory quantum dots are colloidal ZnS/CdSe quantum dots and others colloidal quantum dots.

In the presented invention, the sensory element comprises of nanoporous MC (FIG. 1) infiltrated with emissive sensory organic. Preferably MC may be prepared from p- or n-type Si, by electrochemical etching in hydrofluoric acid/water/ethanol solution. However, other semiconductors from Groups IV, III-V, II-VI can also be used. An example describing the procedure of porous Si MC fabrication is as follows. Briefly, porous Si MCs were prepared by anodic etching of p-type (100)-oriented Si wafers (resistivity ~0.01 Ohm·cm) in 15% solution of HF with ethanol. Anodization was performed under a periodically changing current applied between a silicon wafer and a platinum electrode. In some fabricated samples (FIG. 1), the first DBR consists of 5 periods while the second has 20 periods; each period contains two layers, high (59%) and low (43%) porosity. The low and high porosity layers are fabricated at a current density of 6 mA/cm$^2$ and 25 mA/cm$^2$ respectively followed by MC oxidation at 900° C. under oxygen flow.

The described detector is related to detecting vapors and particulates of different nature including low-vapor pressure nitroexplosives (e.g. TNT, RDX, PETN), chemical warfare agents (e.g. sarin, soman) and other volatile organic and inorganic compounds. However, preferable analytes are low vapor pressure nitroexplosives and their interferants possessing moderate and high vapor pressure. Interferants means non-explosive compounds, which are similar to explosives that could affect the emission of the sensory organics resulting in emission quenching.

Figure 5:
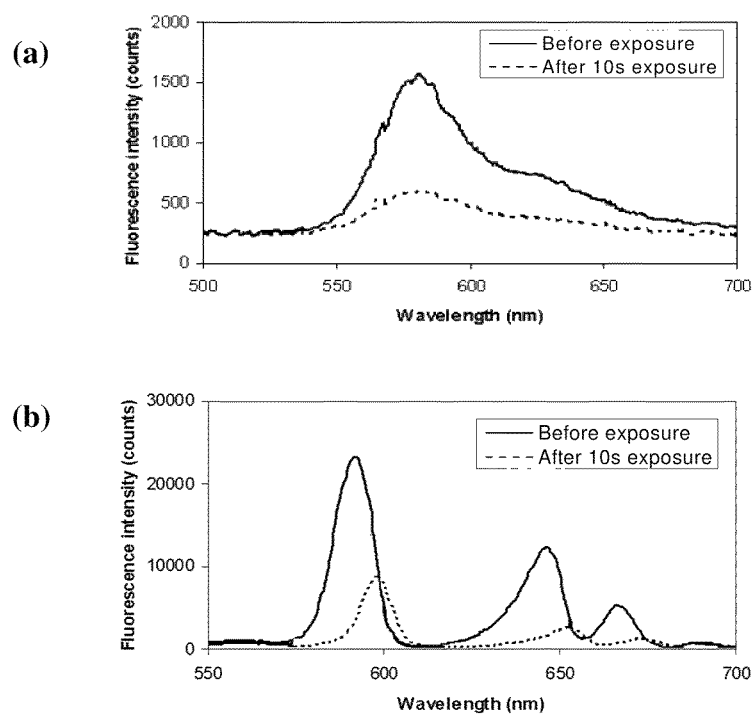
FIG. 5A shows the fluorescence spectral response of polymer MEH-PPV deposited on a flat substrate upon 10 s exposure to nitrotoluene vapors.
FIG. 5B shows the fluorescence spectral response of MC infiltrated with polymer MEH-PPV upon 10 s exposure to nitrotoluene vapors.
Figure 6:
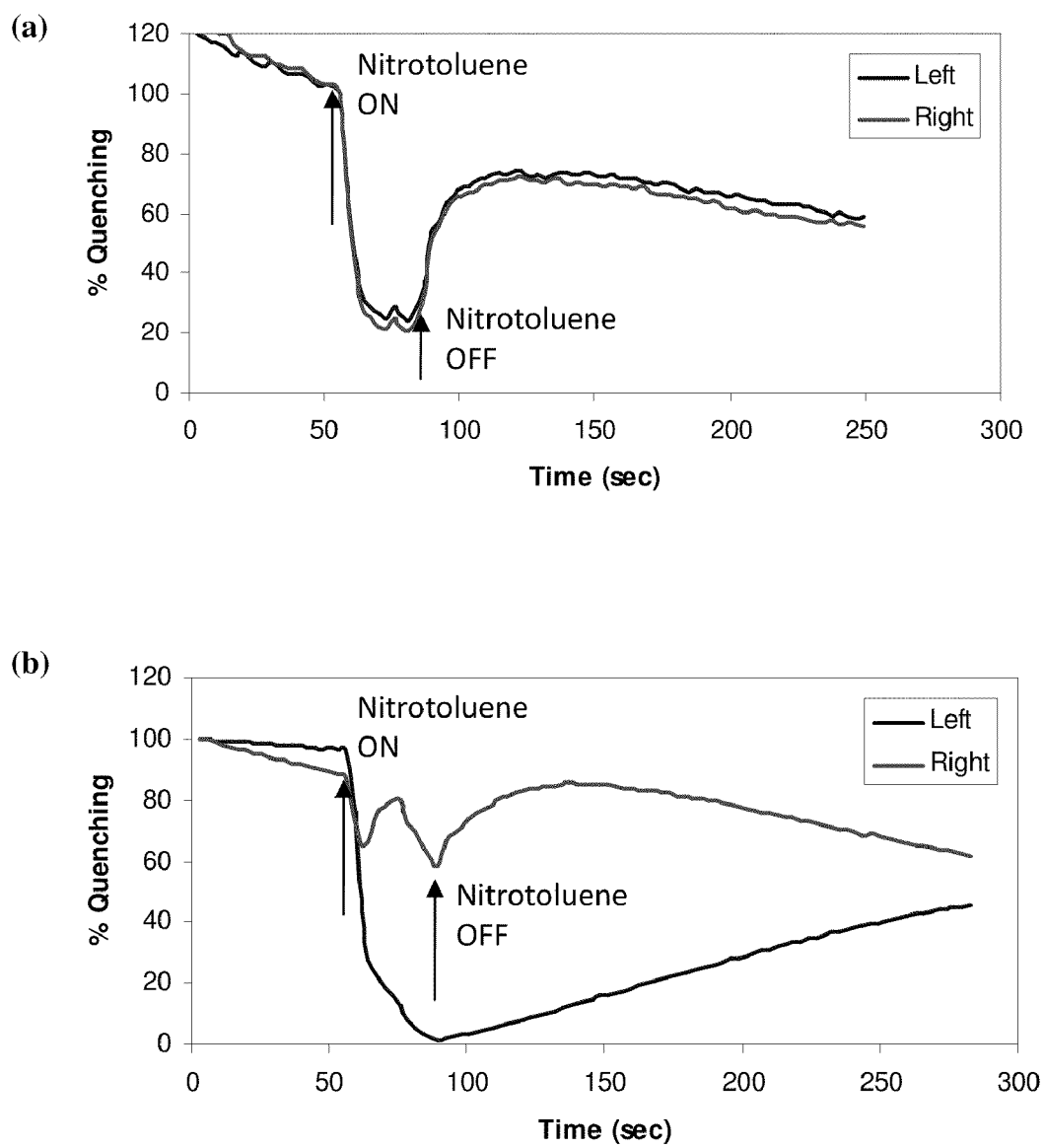
FIG. 6A shows the time traces of the fluorescence intensity taken on the half of the width of broad band of polymer MEH-PPV deposited on a flat substrate for short wavelength/left (blue) and long wavelength/right (red) shoulders upon 25 s exposure to nitrotoluene vapors.
FIG. 6B shows the time traces of the fluorescence intensity taken on the half of the width of MC peak infiltrated with polymer MEH-PPV for short wavelength/left (blue) and long wavelength/right (red) shoulders upon 25 s exposure to nitrotoluene vapors.

In a preferred embodiment, the detector capability to discriminate nitroexplosives from their interferants is demonstrated in FIG. 5. Usually the exposure of SE by explosive vapors (e.g. TNT) results in emission quenching and small (~1 nm or less) spectral shift of MC peak while many non-explosive nitrocompounds with modest or high vapor pressure (e.g. nitrotoluene, nitrobenzene) induce a sizable shift of the MC peak (up to 8-10 nm). The conventional chemosensors with sensory emissive polymer coated on a flat substrate exhibits fluorescence quenching only and does not distinguish between nitrotoluene and TNT, which could likely result in false detection (FIG. 5a). Contrary, porous Si microcavity infiltrated with a sensory polymer shows a spectral shift and fluorescence quenching upon nitrotoluene exposure (FIG. 5b). Thus, nitrotoluene can be easily distinguished from TNT. Further, instead of monitoring the MC spectral shift, a manifold of time traces of the emission intensity detected at different wavelengths can be recorded. The simplest case corresponds to the two time traces recorded at the short wavelength (left) and long wavelength (right) shoulders of MC peak at the half of peak maximum. Upon TNT exposure the difference between time traces will be small (as shift is small); however, upon exposure of nitrotoluene the behavior of these time traces will be significant distinctive due to a large spectral shift (FIG. 6b). In contrast, for conventional sensors (without MC, for polymer on a flat substrate) the time traces taken at two different wavelengths will be the same and similar both for TNT and the nitrotoluene exposure (FIG. 6a) resulting in false positive alarm for nitroexplosive interferants.

Figure 7:
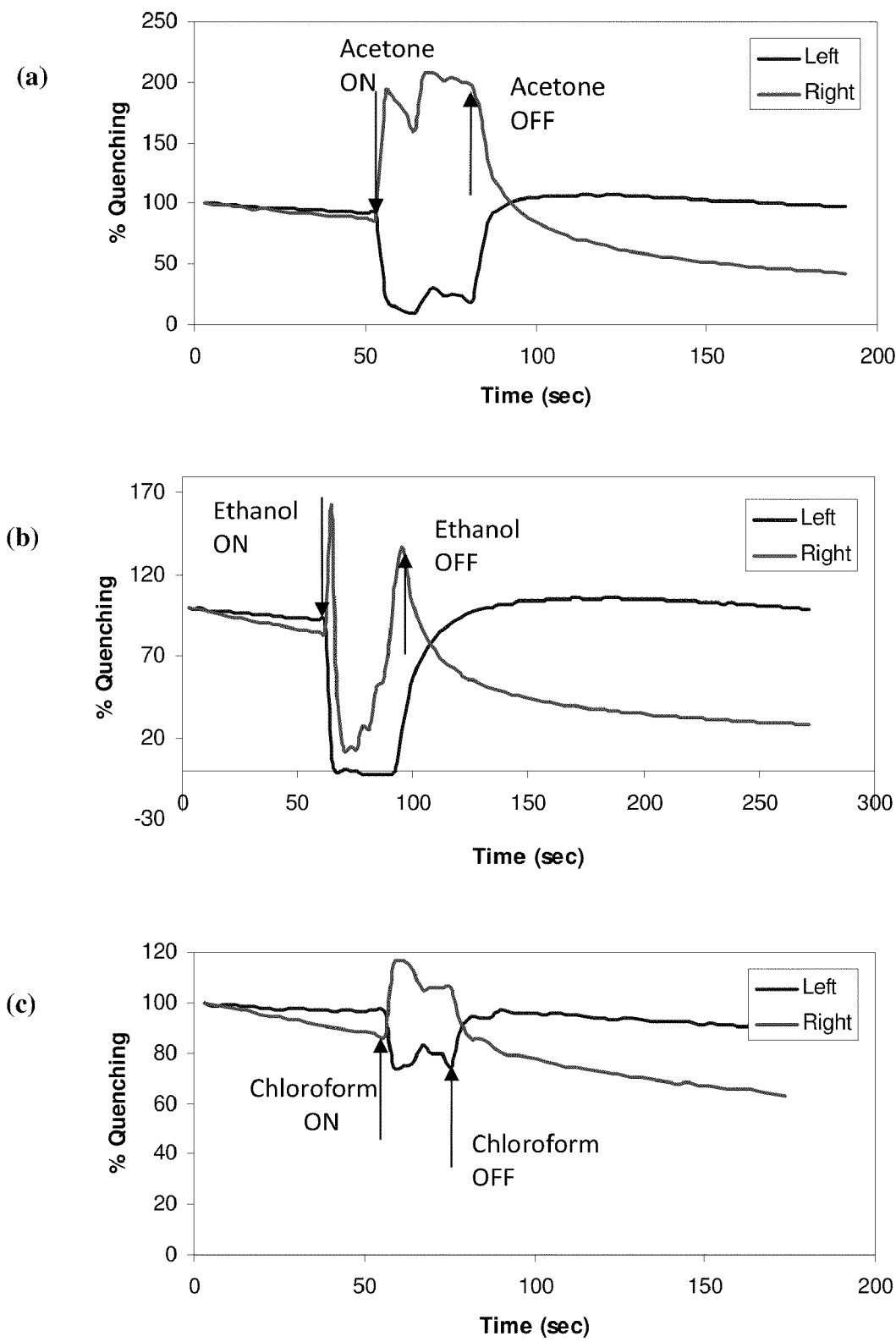
FIG. 7A shows the time traces of the fluorescence intensity taken on the half of the width of MC peak infiltrated with polymer MEH-PPV for short wavelength/left (blue) and long wavelength/right (red) shoulders upon 25 s exposure to acetone vapors.
FIG. 7B shows the time traces of the fluorescence intensity taken on the half of the width of MC peak infiltrated with polymer MEH-PPV for short wavelength/left (blue) and long wavelength/right (red) shoulders upon 25 s exposure to ethanol vapors.
FIG. 7C shows the time traces of the fluorescence intensity taken on the half of the width of MC peak infiltrated with polymer MEH-PPV for short wavelength/left (blue) and long wavelength/right (red) shoulders upon 25 s exposure to chloroform vapors.

In one embodiment, the detector is capable to detect and identify compounds other than explosives vapors and particulates (e.g. CWAs, volatile organic compounds, toxic industrial compounds) because of the precise pattern of the intensity change (quenching/enhancement) and spectral shift (for analyte with moderate and high vapor pressure) associated with target analyte. Such pattern is specific to each analyte and can be stored in the classification database. As was mentioned above, the pattern could be stored in two formats: MC peak maximum intensity change, and its spectral position; either manifold of time traces (at least two) of the MC peak intensity recorded at different wavelengths. FIG. 7 demonstrates the specificity of the pattern for three different analyte vapors: acetone, chloroform and ethanol.

Figure 8:
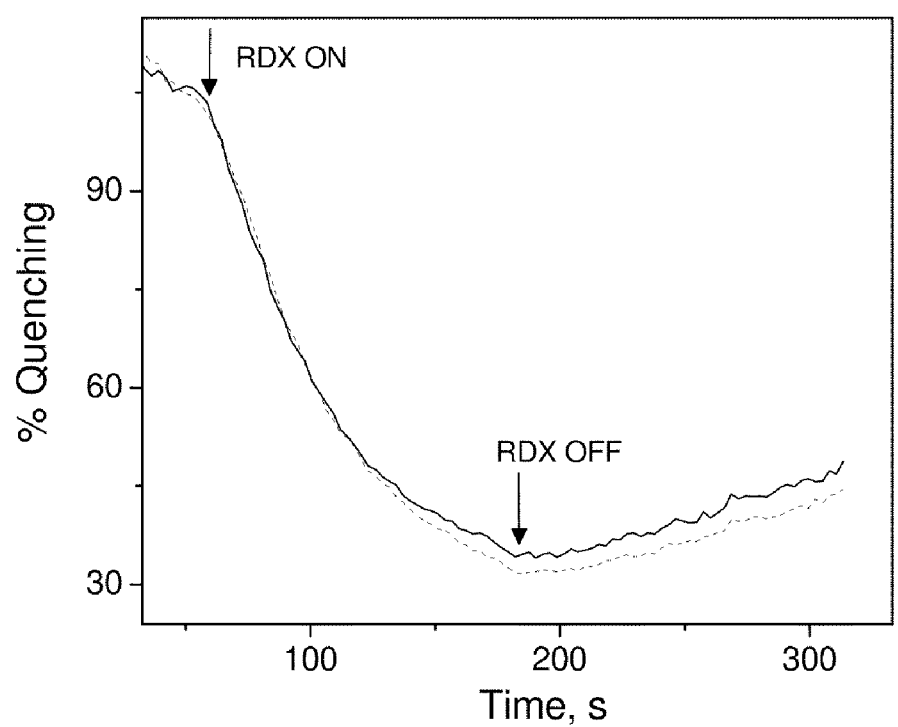
FIG. 8 shows the time traces of the fluorescence intensity taken on the half of the width of MC peak infiltrated with polymer MEH-PPV for short wavelength/left (dashed) and long wavelength/right (solid) shoulders upon exposure of the desorbed RDX from the inspected surface using air-jet heater (surface temperature is 70° C., RDX surface concentration ~75 μg/cm$^2$).

In another embodiment, the air-jet sampling system may be applied to thermally desorp the particulates of the low vapor pressure explosives from the inspected surface. At elevated temperature, particulates can be evaporated resulting in a higher vapor pressure than at normal temperature. Such issue can be critical for detection of nitroexplosives with extremely low vapor pressure such as RDX and PETN (ppt range), when air-jet thermal sampling works in parallel with detecting mode. In fact, only thermal desorption/evaporation allow to detect these analytes. FIG. 8 shows the time traces of the MC emission intensity upon exposure of RDX analyte desorbed from the inspected surface at temperature of 70° C. The surface temperature which is lower than 60-70° C. does not result in RDX detection even at higher surface concentration. Subsequently, by increasing the temperature of the surface (apply more power to heater 32 (FIG. 2)) it is possible to enhance the detector sensitivity.

The preferable material for the flow cell 10 is stainless steel with highly polished inner walls forming the flow channel 11. In some cases flow channel walls can be coated with Teflon if the roughness of the coating is less than that of the polished walls.

The micro-pump, such as KNF UNP09-L provides the air flow through the flow channel, sampling system and inspected area. The flow rate can be regulated in the range of 100-850 ml/min through a digital driver/DAQ/software from the GUI control panel by applying varied DC.

The light source, such as a blue LED from Prizmatix (410 nm), excites the emission of the sensory element through optical fiber 12. The intensity of LED can be regulated through the digital driver/DAQ/software from the GUI control panel in the range of 1-5 mW.

The miniature spectrometer, such as Ocean Optics S 2000, collects the emission from the sensory element through fiber 13 and transfer the spectral-time domain through DAQ 16 to microprocessor 18. Thus, the processing algorithm is capable of operating with time resolve emissive spectra of the SE in the calibration mode (no analyte) and upon analyte exposure). The spectrometer parameters such as integration time, averaging, boxcar can be varied through the digital driver/DAQ/software from the GUI control panel.

What is claimed is:

1. A chemical detector for detecting various chemical compounds and comprising: a sensory element constructed of an organic-inorganic emissive nanocomposite, wherein nanocomposite includes nanoporous periodical semiconducting structure with alternating layers of high and low porosity infiltrated with sensory emissive organics; a flow channel with a pocket incorporating a sensory element; a flow cell for air pumping through a flow channel and air passing over a sensory element; a first optical fiber to excite luminescence of a sensory element and a second fiber to collect luminescence of a sensory element; a miniature spectrometer to analyze an intensity change and spectral shift of narrow luminescence peak upon exposure of analyte containing in the pumping air, processing algorithm to identify and quantify analytes in pumping air; a sampling system functioning in real-time mode to desorb particulates either evaporate them from inspected surface following analytes delivery and multiple cycling over a sensory element.

2. A chemical detector of claim 1, wherein detecting analytes in pumping air belong to the three major groups of analytes: analyte vapors containing in the air; analyte particulates desorbed by a sampling system and delivered with, air to a sensory element; analyte vapors in air, which are result of analyte particulates evaporation affected by a thermal air-jet incorporated in a sampling system.

3. A chemical detector of claim 1, wherein a flow cell comprises the rectangular flow channel connected with micro-pump to provide air pumping through a flow channel.

4. A chemical detector of claim 3, wherein a flow cell comprises a removable cartridge with rectangular pocket for sensory element so that cartridge insertion inside a flow cell aligns or tilts on a small angle the surface of a sensory element with respect to inner walls of a flow channel.

5. A chemical detector of claim 4, further comprising a removable cartridge with a regulated tilt of a pocket to control a sensory element positioning inside a flow channel.

6. A chemical detector of claim 4, wherein removable cartridge incorporates a miniature ultrasound transducer for analyte molecules desorption from a sensory element in recovery mode.

7. A chemical detector of claim 3, wherein a thickness of a flow channel is considerably less than its width and length, at least by the factor of ten or more.

8. A chemical detector of claim 7, wherein inner walls of the flow channel is highly polished to prevent adsorption of analyte molecules on the channel walls.

9. A chemical detector of claim 1, wherein a sensory element comprises nanoporous periodical semiconducting structure constructed from alternating layers of high and low porosity with pore diameter in the range of 5-100 nm infiltrated with sensory emissive organics.

10. A chemical detector of claim 9, wherein a first layer of semiconductor surface has a low porosity to provide a deep infiltration of sensory organics.

11. A chemical detector of claim 9, wherein a deep infiltration results in transformation of a broad luminescence band of emissive sensory organics to a narrow resonance peak due to photon confinement inside periodical semiconductor structure.

12. A chemical detector of claim 9, wherein the spectral position and intensity of luminescent resonance peak are specifically changed upon exposure to analyte molecules.

13. A chemical detector of claim 1, wherein a sampling system comprising the air jet directed to inspected object provides analyte desorbtion and its introduction in a flow channel.

14. A chemical detector of claim 13, wherein air jet functioning at elevated temperatures from 50.degree. C. to 250.degree. C. regulated by a feed back system with assistance of a temperature sensor situated at inlet of a flow channel.

15. A chemical detector of claim 13, wherein air jet is constructed from multi-layer concentric ceramic tubes heated by metal coils.

16. A chemical detector of claim 15, wherein a tube of the smallest diameter in air jet is connected with exhaust of pump to provide multiple analyte cycling through a flow channel with sensory element, smallest tube of the air-jet and inspected area.

17. A chemical detector of claim 15, wherein a tip of air jet is equipped with a focusing/defocusing element allowing to control an area affected by heated air.

18. A chemical detector of claim 13, wherein analyte sampling occurs in real-time mode in parallel with analyte detection due to multiple air cycling.

19. A chemical detector of claim 1, comprising a pump providing air soaking through a flow cell, wherein pump exhaust is connected with inlet of air jet.

20. A chemical detector of claim 1, comprising an optical fiber with one end fixed in a wall of a flow cell under specific angle (between 0 and 90 degree with respect to the normal to a flow direction), and another end connected to light-emitting diode.

21. A chemical detector of claim 1, comprising a miniature optical spectrometer to record temporal responses upon analyte exposure of intensity change and spectral shift of narrow luminescence peak induced by a light interference inside a sensory clement.

22. A chemical detector of claim 21, further comprising an optical fiber to collect the luminescence of a sensory element with one end fixed in a wall of flow cell normally to the flow direction and another end connected to input of a miniature optical spectrometer.

23. A chemical detector of claim 1, comprising software controlling functions of pump, light-emitting device, air jet heater, microprocessor, graphic user interface, data exchange between miniature spectrometer and microprocessor, and running data processing algorithm.

24. A chemical detector of claim 23, further comprising a processing algorithm to analyze output signals and display sign "clear" incase of the absence of target analytes.

25. A chemical detector of claim 23, further comprising processing algorithm to analyze output signals and display sign "analyte X" in case of the presence of analyte X.

26. A chemical detector of claim 25, wherein analyte X is one from group of target analytes, which can be detected by a chemical detector.

27. A chemical detector of claim 23, wherein a data processing algorithm can be based on simple comparative analysis of output digitized signals with data base stored in memory of microprocessor.

28. A chemical detector of claim 23, wherein a data processing algorithm can be pattern recognition algorithm based on statistical or non-statistical methods.

* * * * *